(12) United States Patent
LaBarge et al.

(10) Patent No.: US 6,709,558 B2
(45) Date of Patent: Mar. 23, 2004

(54) GAS SENSOR

(75) Inventors: William J. LaBarge, Bay City, MI (US); Eric J. Detwiler, Davison, MI (US); Paul C. Kikuchi, Fenton, MI (US); Richard F. Beckmeyer, Davisburg, MI (US)

(73) Assignee: Delphi Technologies, Inc., Troy, MI (US)

( * ) Notice: Subject to any disclaimer, the term of this patent is extended or adjusted under 35 U.S.C. 154(b) by 23 days.

(21) Appl. No.: 10/141,548

(22) Filed: May 8, 2002

(65) Prior Publication Data

US 2003/0209433 A1 Nov. 13, 2003

(51) Int. Cl.⁷ .............................................. G01N 27/407
(52) U.S. Cl. ........................ 204/429; 204/424; 73/23.32
(58) Field of Search ................................ 204/429, 428, 204/424; 73/23.32

(56) References Cited

U.S. PATENT DOCUMENTS

| | | | | |
|---|---|---|---|---|
| 4,217,038 A | | 8/1980 | Letter et al. | |
| 4,345,985 A | * | 8/1982 | Tohda et al. | 204/192.15 |
| 4,915,814 A | * | 4/1990 | Harada et al. | 204/425 |
| 5,486,279 A | * | 1/1996 | Friese et al. | 204/429 |
| 5,492,612 A | * | 2/1996 | Kennard et al. | 204/429 |
| 6,132,564 A | | 10/2000 | Licata | |
| 6,210,552 B1 | | 4/2001 | Mizutani et al. | 204/429 |
| 6,287,986 B1 | | 9/2001 | Mihara | |

* cited by examiner

*Primary Examiner*—Kaj K. Olsen
(74) *Attorney, Agent, or Firm*—Jimmy L. Funke

(57) ABSTRACT

Disclosed herein is a gas sensor and a method of making a gas sensor comprising disposing a reference electrode on an inner surface of an electrolyte; sputtering a sensing electrode on an outer surface of the electrolyte; sputtering a zirconia layer on a side of the sensing electrode opposite the electrolyte, wherein the zirconia layer has a thickness of about 20 nanometers to about 1 micrometer, and disposing a protective layer on a side of the zirconia layer opposite the sensing electrode.

14 Claims, 1 Drawing Sheet

GAS SENSOR

BACKGROUND

Automotive vehicles with an internal combustion engine have an exhaust system including a pathway for exhaust gas to move away from the engine. Depending on the desired operating state, internal combustion engines can be operated with fuel/air ratios in which (1) the fuel constituent is present in a stoichiometric surplus (rich range), (2) the oxygen of the air constituent is stoichiometrically predominant (lean range), and (3) the fuel and air constituents satisfy stoichiometric requirements. The composition of the fuel-air mixture determines the composition of the exhaust gas. In the rich range, considerable quantities of nonburned or partially burned fuel are found, while the oxygen has been substantially consumed and has nearly disappeared. In the lean range, the ratios are reversed, and in a stoichiometric composition of the fuel-air mixture, both fuel and oxygen are minimized.

It is well known that the oxygen concentration in the exhaust gas of an engine has a direct relationship to the air-to-fuel ratio of the fuel mixture supplied to the engine. As a result, gas sensors, namely oxygen sensors, are used in automotive internal combustion control systems to provide accurate oxygen concentration measurements of automobile exhaust gases. They are used for determination of optimum combustion conditions, maximization of fuel economy, and management of exhaust emissions.

A switch type oxygen sensor, generally, comprises an ionically conductive solid electrolyte material, a sensing electrode that is exposed to the exhaust gas, and reference electrode that is exposed to a reference gas. Reference gases including air or oxygen, at known partial pressures are used. The sensor operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right) \ln\left(\frac{P_{O_2}^{ref}}{P_{O_2}}\right)$$

where:
  E=electromotive force
  R=universal gas constant
  F=Faraday constant
  T=absolute temperature of the gas
  $P_{O_2}^{ref}$=oxygen partial pressure of the reference gas
  $P_{O_2}$=oxygen partial pressure of the exhaust gas The presence of a large oxygen partial pressure difference between rich and lean exhaust gas conditions creates a step-like difference in cell output at the stoichiometric point; the switch-like behavior of the sensor enables engine combustion control about stoichiometry. Stoichiometric exhaust gas, which contains unburned hydrocarbons, carbon monoxide, and oxides of nitrogen is a favored condition because these materials can be converted very efficiently to water, carbon dioxide, and nitrogen by automotive three-way catalysts in automotive catalytic converters. Also, in addition to their value for emissions control, the sensors provide improved fuel economy and drivability.

Further control of engine combustion can be obtained using amperometric mode exhaust sensors, where oxygen is electrochemically pumped through an electrochemical cell using an applied voltage. A gas diffusion-limiting barrier may be used to create a current limited output, the level of which is proportional to the oxygen content of the exhaust gas. These sensors typically consist of two or more electrochemical cells; one of these cells operates in potentiometric mode and serves as a reference cell, while another operates in amperometric mode and serves as an oxygen-pumping cell. This type of sensor, known as a wide range or linear air/fuel ratio sensor, provides information beyond whether the exhaust gas is qualitatively rich or lean; it can quantitatively measure the air/fuel ratio of the exhaust gas.

Due to increasing demands for improved fuel utilization and emissions control, more recent emphasis has been on wide range oxygen sensors capable of accurately determining the oxygen partial pressure in exhaust gas for internal combustion engines operating under both fuel-rich and fuel-lean conditions. Such conditions require an oxygen sensor that is capable of rapid response to changes in oxygen partial pressure by several orders of magnitude, while also having sufficient sensitivity to accurately determine the oxygen partial pressure in both the fuel-rich and fuel-lean conditions. One way to obtain such sensors is by providing temperature compensation to the sensor.

The temperature of the exhaust gases ranges from ambient temperature, when the engine has not been run recently, to higher than 1,000° C. Since air-fuel ratio output signal depends largely on the exhaust gas temperature, temperature compensation is needed. A heater assists an oxygen sensor in making more precise measurements over a wide range of exhaust gas temperatures, especially when the exhaust gas temperature is low. The addition of the heater also helps to decrease the light-off time of the sensor, that is, the time that it takes for the sensor to reach the minimum temperature for proper operation.

Reduction of light-off times has been accomplished through the use of high power heaters. One method for further decreasing light-off times while using only small or modest heating power, is to substantially decrease the size of the sensing element, especially the electrolyte. Similarly, during low temperature operation (e.g., about 350° C. or less), the switching time, or time required for the sensor to detect a change from rich to lean or lean to rich exhaust gas compositions, must be as low as possible, preferably below about half a second (500 milliseconds).

The surface geometry and the availability of the electrode to the exhaust gas is a factor that affects the sensitivity and response time of an exhaust gas sensor. Also, the thinner the electrolyte, and the more porous the electrode, the more rapid and more sensitive is the sensor. Planer sensors offer a benefit of large surface area, while affording the possibility of a relatively thin electrolyte. A method of making gas sensor that would allow for accurate determination of the oxygen content in an exhaust gas would be useful.

SUMMARY

Disclosed herein is a method of making a gas sensor, comprising disposing a reference electrode on an inner surface of an electrolyte, sputtering a sensing electrode on an outer surface of the electrolyte, sputtering a zirconia layer on a side of the sensing electrode opposite the electrolyte, wherein the zirconia layer has a thickness of about 20 nm to about 1,000 nm, and disposing a protective layer on a side of the zirconia layer opposite the sensing electrode.

Also disclosed is a gas sensor, comprising a reference electrode deposited on an inner surface of an electrolyte, a sensing electrode sputtered on an outer surface of the electrolyte, a zirconia layer sputtered on a side of the sensing electrode opposite the electrolyte, wherein the zirconia layer has a thickness of about 20 nanometers to about 1,000 nm; and a protective layer deposited on a side of the zirconia layer opposite the sensing electrode. These and other features will be apparent from the following brief description of the drawings, detailed description, and attached drawings.

In addition, disclosed is a method of making a gas sensor, comprising disposing a reference electrode on an inner surface of an electrolyte, sputtering a sensing electrode comprising platinum and aluminum, optionally comprising ruthenium, rhodium or a combination comprising one of the foregoing on an outer surface of the electrolyte, wherein the sputtering comprises xenon, neon, or a combination comprising one of the foregoing, and wherein the temperature of the electrolyte is less than or equal to about −80° C. during at least a portion of the sputtering, xenon ion cleaning the sensing electrode, etching the sensing electrode with an etching solution having a pH greater than 7, heat-treating at a temperature of about 400° C. to about 1200° C., sputtering a zirconia layer on a side of the sensing electrode opposite the electrolyte, wherein the zirconia layer has a porosity of about 2 vol % to about 8 vol %, based on the total volume of the zirconia layer, and disposing a protective layer on a side of the zirconia layer opposite the sensing electrode, wherein the protective layer has a porosity of about 30 vol % to about 60 vol %, based on the total volume of the protective layer.

BRIEF DESCRIPTION OF THE DRAWINGS

Referring now to the following FIGURE, in which.

DETAILED DESCRIPTION

Figure 1:
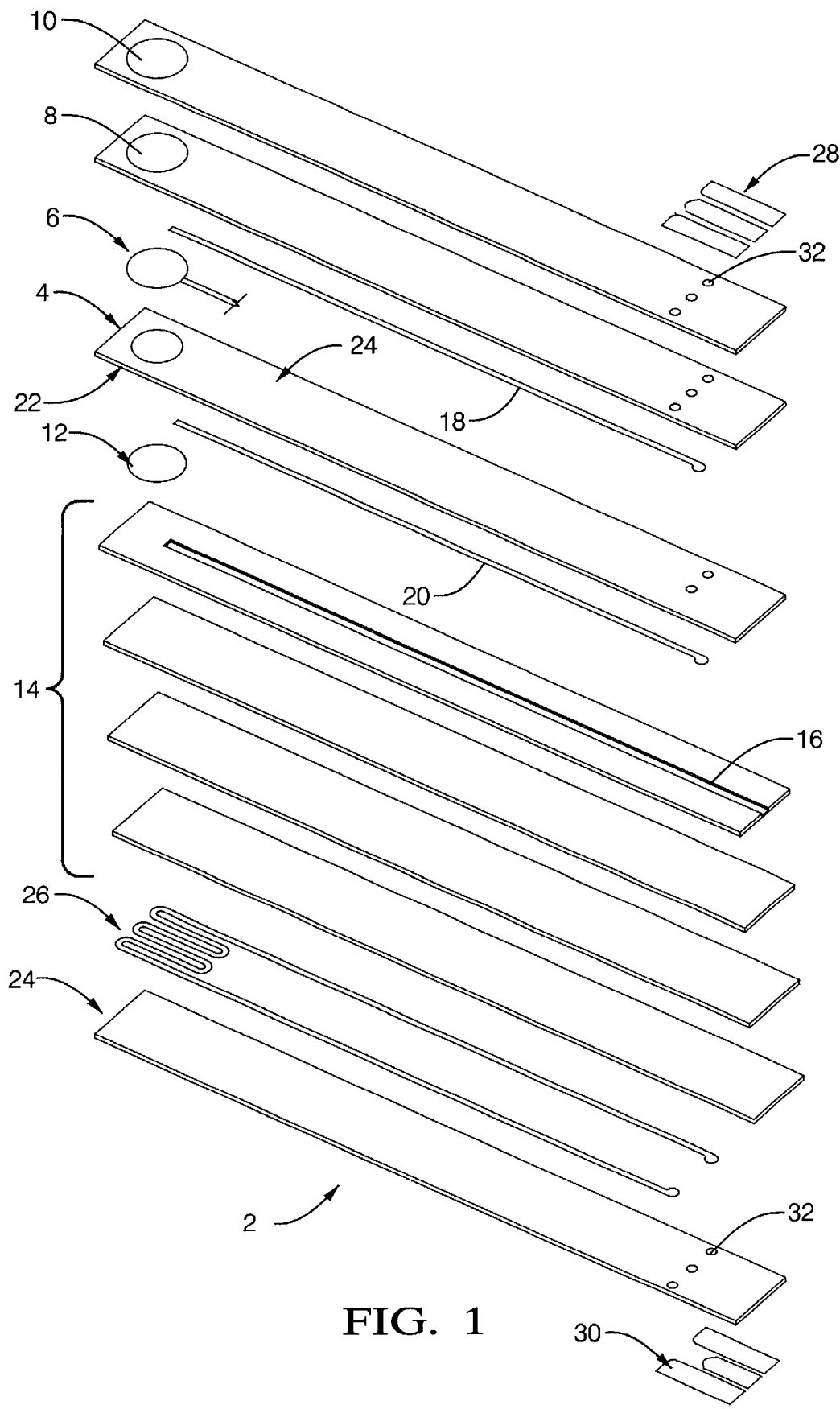
FIG. 1 is an exploded view of a general flat plate type oxygen sensor.

Although described in connection with an oxygen sensor, it is to be understood that the gas sensor could be sensitive to other analytes of interest in gas, such as, for example, nitrogen oxides, hydrogen, hydrocarbons, and the like. Furthermore, while oxygen is the reference gas used in the description disclosed herein, it should be understood that other gases could be employed as a reference gas.

FIG. 1 represents one embodiment of the sensor. FIG. 1 shows a sensor (2) with an ionically conductive electrolyte (4) having an inner side (22) and an outer side (24). A sensing electrode (6) is disposed on the outer side (24) of the electrolyte (4), between, and in fluid communication with the electrolyte (4) and a zirconia layer (8). On a side of the zirconia layer (8), and in fluid communication with the zirconia layer (8), is a protective layer (10). On the inner side (22) of the electrolyte (4) is a reference electrode (12). The inner side (22) of the electrolyte (4) may have support layer(s) (14) containing a reference gas channel (16) in fluid communication with the reference electrode (12). Disposed in electrical communication with the sensing electrode (6) is a first electrical lead (18), while disposed in electrical communication with the reference electrode (10) is a second electrical lead (20). Optionally, in thermal communication with the inner side (22) of the electrolyte (4) is a heater (26). Finally, in electrical communication with the electrodes (6,12), the leads (18,20), heater (26), and vias (32) are contacts (28, 30). A second zirconia layer (not shown) may also be formed on the second side of the reference electrode (12). Additionally, other sensor components may be employed such as a pumping cell, reference chamber, lead gettering layer, ground plane, porous electrolyte, and the like.

The support layers (14, 24, 34, 36), heater (26), contacts (28, 30) and leads (18,20), can comprise materials capable of use in the sensor environment. For an oxygen sensor, the materials are capable of use at the elevated temperatures and preferably at operational conditions found in vehicle exhaust systems. For example, the support layers (14, 24, 34, 36) can comprise a dielectric material such as a metal oxide, e.g., alumina, and the like, while the heater (26), contacts (28, 30) and leads (18,20) can comprise a thermally and electrically conductive metal such as platinum, palladium, ruthenium, and the like, and other metals, metal oxides, alloys and mixtures comprising at least one of the foregoing metals.

The electrolyte (4), which is preferably a solid electrolyte, can be formed of any material that is capable of permitting the electrochemical transfer of oxygen ions. Suitable electrolyte materials can comprise metal oxides (such as zirconia, and the like), which may optionally be stabilized with calcium, barium, yttrium, magnesium, aluminum, lanthanum, cesium, gadolinium, and the like, as well as oxides, alloys, and combinations comprising at least one of the foregoing electrolyte materials. For example, the electrolyte can be alumina and yttrium stabilized zirconia.

Disposed adjacent to the electrolyte (4) are electrodes (6,12). Both the sensing electrode (6), which is exposed to the exhaust gas during operation, and the reference electrode (12), which is exposed to a reference gas, preferably have a porosity sufficient to permit diffusion of oxygen ions therethrough. These electrodes can comprise any metal capable of ionizing oxygen, including, but not limited to, noble metals such as platinum, palladium, gold, osmium, rhodium, iridium and ruthenium; and metal oxides, such as zirconia, yttria, ceria, calcia, alumina, and the like; as well as alloys and combinations comprising at least one of the foregoing metals and metal oxides.

The durability of the electrode typically improves with increasing thickness; however, it is preferred that the thickness be controlled, particularly with using thin film techniques, so as not to bridge and therefore block-in the pores to thereby preclude free access of the reference gas to the sensor. Porosity can be enhanced by the addition of particulate organic materials such as, for example, organic polymers, microballoons, cornstarch, and other fugitive materials that are subsequently removed. Cost factors may also present a factor in determining the thickness desired.

The reference electrode may be disposed on the inner surface (22) of electrolyte (4) by depositing a suitable material on the exposed surface using thin or thick film deposition techniques. Examples of suitable thin film deposition techniques include chemical vapor deposition, printing (screen printing, pad printing, ink jet printing, and the like), sputtering, stenciling, spraying (e.g., electrostatically spraying, slurry spraying, plasma spraying, and the like), painting, and the like, as well as combinations comprising at least one of the foregoing techniques. The preferred reference electrode is a pure platinum sputtered layer covered with a dense plasma sprayed layer.

The thickness of the reference electrode is about 0.4 micrometers to about 8 micrometers. Preferably within this range, the thickness of the reference electrode is greater than or equal to about 1.0 micrometer, more preferably greater than or equal to about 1.6 micrometers. Also within this range, the thickness is preferably less than or equal to about 2.5 micrometers, more preferably less than or equal to about 2.0 micrometers, depending upon the application method and durability requirements.

Disposed on the outer side (24) of the electrolyte (4) is the sensing electrode (6). Due to the sensing electrode's exposure to exhaust gases, e.g., when employed in a vehicle exhaust system, the sensing electrode (6) preferably further comprises a material responsive to the presence of nitrogen oxides ($NO_x$) in the exhaust gas. Suitable materials include ruthenium and rhodium. Ruthenium oxide ($RuO_2$) and rhodium oxide are much more stable than platinum oxide or palladium oxide. $RuO_2$ is more stable at higher temperatures allowing $NO_x$ activity at higher measuring temperatures than can be achieved with electrodes having only platinum.

Although the sensing electrode (6) can be disposed on the electrolyte (4) via the techniques employed for the reference electrode (12), the sensing electrode is preferably sputtered onto the electrolyte (4). Various types of sputtering can be employed as well as various sputtering targets, with xenon gas (Xe) sputtering preferred.

For efficient sputtering, it is preferred to use the highest mass noble gas that has less mass than the target element. For example, for platinum deposition, xenon gas is greatly preferred. For aluminum deposition, neon gas is especially preferred. For yttrium and zirconium, krypton gas is especially preferred. Since platinum has a very high mass, neon is not effective for sputtering platinum, yttrium, or zirconium. Yet, since aluminum has a low mass, xenon and krypton are not very effective at sputtering aluminum. For a mixed sputtering target of platinum and aluminum, a mixture of xenon and neon are preferred to produce the electrode.

With mixed xenon and neon gasses, the energy required for vaporization is minimized, detrimental effects such as multiple layer growth are greatly reduced or eliminated, and diameters of particles are reduced. Also, less strain is observed in the layers, stronger electrode-substrate interaction is obtained, defects such as hillocks and pinholes are greatly reduced, and the compressive stresses of the lattice are reduced. The micro-hardness of the electrode is also less, indicating more electrode surface area.

It has also been found that Xe sputtering deposition deposits finer particles of platinum, aluminum oxide, yttrium-zirconium oxide and the like compared to other types of deposition processes. As such, particles of platinum are more intimately mixed with particles of ruthenium, aluminum, yttrium-zirconium, and the like. More intimate mixing increases electrode durability and high temperature oxidation and hot corrosion resistance is also improved. Electrode activity is greater because electrodes are not exposed to temperatures greater than 900° C. (as opposed to cofired electrodes that are heated to 1500° C.). Also, sputtered electrodes are not exposed to poisons such a $SiO_2$.

In one embodiment, a sensing electrode (6) can be sputtered onto the electrolyte (4) using a sputtering target comprising platinum, aluminum, and optionally ruthenium, rhodium, or a combination comprising at least one of the foregoing. Preferably, the sputtering target comprises platinum at a concentration of about 96 wt % to about 100 wt %. Preferably within this range, the platinum concentration in the sputtering target is greater than or equal to about 97 wt %, more preferably greater than or equal to about 98 wt % platinum based upon the total weight of the target. Also, within this range the concentration of platinum in the sputtering target is preferably less than or equal to about 99 wt %, more preferably less than or equal to about 98.5 wt % platinum based on the total weight of the target.

The sputtering target also may comprise aluminum at a concentration of about 0.1 wt % to about 4 wt % based on the total weight of the target. Preferably, the concentration of aluminum in the sputtering target is less than or equal to about 3 wt %, more preferably less than or equal to about 1.8 wt % aluminum based upon the total weight of the target. Also within this range greater than or equal to about 0.2 wt % preferred, with greater than or equal to about 1 wt % more preferred.

The sputtering target may also comprise ruthenium (Ru), rhodium (Rh), or a mixture comprising at least one of the foregoing, at a concentration of less than or equal to about 2 wt % based on the total weight of the target. Preferably within this range, the concentration of ruthenium, rhodium, or a mixture comprising at least one of the foregoing in the sputtering target is less than or equal to about 1 wt %, more preferably less than or equal to about 0.2 wt % based upon the total weight of the target. Also within this range, the concentration of Ru, Rh, or a mixture comprising at least one of the foregoing in the sputtering target of greater than or equal to about 0.01 wt % is preferred, with greater than or equal to about 0.1 wt % more preferred.

The sputtering conditions are controlled in order to obtain a sensing electrode having the desired composition, particle size, porosity, and thickness. The sensing electrode has a platinum concentration of about 96 wt % to about 99.9 wt % based on the total weight of the electrode. Preferably within this range, the platinum concentration is greater than or equal to about 97 wt %, more preferably greater than or equal to about 98 wt % based on the total weight of the electrode. Also within this range, the platinum concentration is preferably less than or equal to about 99 wt %, more preferably less than or equal to about 98.5 wt % based on the total weight of the electrode. Prior to etching, the sensing electrode has an aluminum concentration of about 0.1 wt % to about 4 wt % based on the total weight of the electrode. Preferably within this range, the aluminum concentration is greater than or equal to about 0.2 wt %, more preferably greater than or equal to about 1 wt % based on the total weight of the electrode. Also within this range, the aluminum concentration is preferably less than or equal to about 3 wt %, more preferably less than or equal to about 2 wt % based on the total weight of the electrode. The sensing electrode can have a ruthenium and/or rhodium concentration of about 0 wt % to about 2 wt % based on the total weight of the electrode. Preferably within this range, the ruthenium and/or rhodium concentration is greater than or equal to about 0.1 wt %, more preferably greater than or equal to about 0.5 wt % based on the total weight of the electrode. Also within this range, the ruthenium and/or rhodium concentration is preferably less than or equal to about 1.5 wt %, more preferably less than or equal to about 1 wt % based on the total weight of the electrode.

The sensing electrode has a thickness of about 0.1 micrometers to about 10 micrometers. Preferably within this range, the sensing electrode has a thickness greater than or equal to about 0.4 micrometers, more preferably greater than or equal to about 1.0 micrometer. Also within this range, the thickness is preferably less than or equal to about 6 micrometers, more preferably less than or equal to about 4 micrometers.

A sensor is heated up and then cooled millions of times during service life. Little by little, the platinum pulls away from the spinel protective layer. Samples that have been aged under very hot temperatures (greater than 900° C.) and under rich conditions, can be separated by hand, wherein the platinum comes off the sensor as a thin foil. To enhance adhesion of the sensing electrode (6) to the electrolyte (4), the electrolyte (4) can be cooled below ambient temperature (i.e., less than 25° C.) during at least a portion of the sputtering process. By cooling the electrolyte (4) during sputtering, an electrode having reduced stress between the electrode layer (6) and the electrolyte (4) is achieved. This is believed to result because when platinum is deposited on yttrium-zirconium electrolyte, there is a thermal expansion mismatch with the different materials. During sputtering, the temperature of the electrolyte can be reduced to less than or equal to about −80° C. (80 degrees below zero Celsius) with less than or equal to about −200° C. preferred to improve adhesion of the sensing electrode.

Once the sensing electrode (6) is sputtered onto the outer surface (24) of the electrolyte (4), the surface of the electrode may be ion cleaned, preferably with noble gas ions. This step can take place before or after heat treatment (i.e., annealing, calcination and the like). Before the heat treatment is greatly preferred however, for simple process flow. One method of ion cleaning is with xenon (Xe) ion cleaning, xenon is preferred because it can eject heavy platinum atoms with the least amount of energy applied. Cleaning is also important because at the triple point (i.e., the junction where platinum, exposed yttria stabilized zirconia (YSZ) and exhaust gas interact), the sputtered electrode can be so dense that Pt covers the entire surface, and does not allow gas to access the exposed YSZ. The electrode layer has to have porosity to function properly. Xenon ion cleaning can eject platinum particles as large as about 8 nm that could otherwise inhibit activity. Other ionized gasses could be used in cleaning, however, xenon is the heaviest and thus a more efficient noble gas for this purpose, and as such, Xe is more preferred.

Once the sensing electrode (6) is deposited on the electrolyte, the electrode (6) is preferably subject to basic etching to remove the aluminum deposited during the sputtering process. During etching, the sensing electrode (6) is contacted with a basic etching solution (i.e., pH greater than 7) that preferably comprises a metallic hydroxide. Suitable metallic hydroxides, including sodium hydroxide, lithium hydroxide, magnesium hydroxide, potassium hydroxide, cesium hydroxide, barium hydroxide, strontium hydroxide, calcium hydroxide, tetramethyl ammonium hydroxide, and the like, as well as combinations comprising at least one of the foregoing metal hydroxides, with potassium hydroxide being more preferred. The etching solution also preferably comprises a $C_1$–$C_4$ alcohol, such as propanol, iso-propanol, and the like, as well as combinations comprising at least one of the foregoing alcohols.

A preferred etching solution comprises potassium hydroxide (KOH) in a mixture of water and iso-propanol such that a concentration of KOH is about 0.1 moles per liter (M) to about 1.0 M. Preferably within this range, the concentration of KOH is greater than or equal to about 0.5 M. The iso-propanol concentration is preferably greater than or equal to about 15 volume percent (vol %), with a concentration of iso-propanol greater than or equal to about 25 vol % preferred, base upon the total volume of the etching solution. Also, the iso-propanol concentration in the etching solution is preferably less than or equal to about 50% based on the total volume of the etching solution (over 50% isopropanol inhibits the etching). The duration of the etching treatment, which can range from several minutes to several hours, is dependent upon the pH and temperature of the solution. The temperature of the solutions can range from ambient (e.g., about 25° C.) to boiling. In order to simplify temperature control of the solutions and process time requirements, the solutions are preferably maintained at a temperature of greater than or equal to about 40° C. and a pH of greater than or equal to about 9.3.

The average particle or grain size of the sensing electrode material is about 2 nanometers (nm) to about 20 nm, as measured along a major axis. Preferably within this range, the average grain size is greater than or equal to about 6 nm, more preferably greater than or equal to about 8 nm. Also within this range, the average particle or grain size of the remaining sensing electrode material is preferably less than or equal to about 12 nm, more preferably less than or equal to about 9 nm as measured along a major axis.

The sensor may be heat-treated, also known as being annealed and/or calcined, to strengthen the surface of the sensor. Heat-treating includes heating the sensor to a temperature of about 400° C. to about 1200° C. Within this temperature range, a temperature of greater than or equal to about 700° C. is preferred, with a temperature of greater than or equal to about 800° C. more preferred. Also preferred within this temperature range is a temperature of less than or equal to about 900° C. The time period can vary from minutes to hours, depending upon the temperature. Preferably, the period of time for heat treatment is sufficient to devitrify any amorphous glassy layer (on the sensing electrode, electrolyte, and/or at the electrode-electrolyte interface), to convert the glassy layer to an aqueous soluble layer, and to incorporate a small amount of various salts into the sensor structure to improve electrocatalytic activity and thus sensor function.

After heat treatment, the sensor is preferably washed (e.g., in an alkaline solution). The alkaline cleaner in the solution can comprise carbonates, alkalis (e.g., metal hydroxides ($R(OH)_a$), metal carbonates ($R_aCO_3$) and the like, as well as combinations comprising at least one of the foregoing; wherein a is 1 or 2, and wherein R is sodium, lithium, magnesium, potassium, cesium, barium, strontium, calcium, and the like, as well as combinations comprising at least one of the foregoing. Preferably, the alkaline cleaner solution is prepared from sodium carbonate ($Na_2CO_3$), potassium carbonate ($K_2CO_3$), sodium hydroxide (NaOH), potassium hydroxide (KOH), or combinations comprising at least one of the foregoing.

The concentration of the alkaline cleaner in the cleaner solution depends on the time and temperature of treatment. Typically, the concentration is about 1 wt % to about 20 wt % cleaner, (i.e., carbonate, alkali, or combination comprising at least one of the foregoing materials) based on the total weight of the solution. Preferably within this range, the cleaner concentration is greater than or equal to about 2 wt %, with the balance of the solution being solvent (e.g., water or the like). Also within this range, the concentration is preferably less than or equal to about 15 wt % cleaner, more preferably less than or equal to about 10 wt % cleaner based on the total amount of solution. For example, about 2 wt % to about 5 wt % boiling alkaline solution adequately washes a sensor element in up to about an hour, with between about 1 to about 45 minutes preferred, and at least about 5 minutes time more preferred. The boiling solution is used to illustrate the process because it simplifies the temperature control requirements, and shows hot solutions work efficiently and save time.

Optionally, between the solution treatments and after the alkaline solution wash, the sensor can be rinsed with water, preferably deionized water. Finally, the sensor can be dried in a temperature of ambient to a temperature that will not adversely affect the sensor components. To facilitate drying, the sensor is preferably dried at a temperature of about 700° C. to about 900° C. Within this range, the temperature is preferably greater than or equal to about 750° C. Also within this range, the temperature is preferably less than or equal to about 850° C. Furthermore, it is preferred to dry the sensor under an inert atmosphere (e.g., nitrogen, argon, carbon dioxide, and the like), as well as combinations comprising at least one of the foregoing inert atmospheres.

Once the sensing electrode (6) is deposited and optionally cleaned, a zirconia layer (8) is then disposed over the sensing electrode. This zirconia layer allows for absorption of hydrogen that comes through the layers faster than any of the other gasses. The hydrogen is consumed by zirconia being reduced without generating any electric signal. While other reducible oxides exist, zirconia is greatly preferred because of the thermal expansion match. This zirconia layer preferably comprises a stabilizer. Possible stabilizers include various metal oxides such as oxides of calcium, barium, yttrium, magnesium, aluminum, lanthanum, cesium, gadolinium, and the like, as well as combinations comprising at least one of the foregoing metal oxides, with an oxide of yttria preferred. The preferred final composition is 4 mol % yttrium oxide-zirconia ($Y_2O_3$—$ZrO_2$).

In order to attain a thin zirconia layer (i.e., less than or equal to about 1 micrometer) the zirconia layer is preferably sputtered onto the surface of the sensing electrode. Suitable conditions for the sputtered deposition of the zirconia layer include a zirconium-yttrium (Zr—Y) alloy target comprising about 17.8 wt % Y and about 82.2 wt % Zr. The zirconia layer (8) is deposited to a thickness of about 20 nm to about 1,000 nm (1 micrometer). Preferably within this range, the zirconia layer (8) is deposited to a thickness less than or equal to about 100 nm. Also within this range, the zirconia layer (8) is preferably deposited to a thickness greater than or equal to about 50 nm. A thickness above about 1 micrometer adds difficulty with adhesion of the spinel poison protective layer.

The porosity of the zirconia layer (8) is greater than or equal to about 2 vol %. Preferably, the porosity of the zirconia layer (8) is greater than or equal to about 4 vol %, more preferably greater than or equal to about 8% by total volume. The thinner the zirconia layer, the less significant is the "lean shift" observed during operation.

After disposing the zirconia layer (8) over the sensing electrode (6), a protective layer (10) can be disposed over the side of the zirconia layer (8) opposite the sensing electrode (6). This protective layer (10) protects the sensing electrode (6) from impurities that cause poisoning of that electrode. The protective layer can comprise various layers of spinel (e.g., magnesium aluminate), alumina, zirconia, and the like, as well as combinations comprising at least one of the foregoing materials. For example, a first protective layer is preferably less than or equal to about 4% porosity by volume, and a second layer is preferably about 30% to about 60% porosity by volume. Within this range, the second layer porosity is preferably greater than or equal to about 50 vol %. Also for example, the thickness of the first layer is preferably less than or equal to about 100 nm, and the second layer is about 140 micrometers to about 240 micrometers.

As described above, exhaust sensors provide feed back information that is important for improving the efficiency and performance of a vehicle. The planer sputtered exhaust sensor described herein has improved accuracy, reliability, and reproducibility. It also provides faster functioning of the sensor (measures at a lower temperature), produces a cleaner electrical signal, a more accurate sensor signal, and has longer electrode life than other sensors.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A gas sensor, comprising:
    a reference electrode deposited on an inner surface of an electrolyte;
    a sensing electrode sputtered on an outer surface of the electrolyte;
    a zirconia layer sputtered on a side of the sensing electrode opposite the electrolyte, wherein the zirconia layer has a thickness of about 20 nm to about 1,000 nm; and
    a protective layer deposited on a side of the zirconia layer opposite the sensing electrode.

2. The gas sensor of claim 1, wherein the zirconia layer further comprises zirconia and an additional metal oxide.

3. The gas sensor of claim 2, wherein the additional metal oxide is selected from the group consisting of yttria, calcia, alumina, ceria, and combinations comprising at least one of the foregoing metal oxides.

4. The gas sensor of claim 2, wherein the additional metal oxide comprises yttria.

5. The gas sensor of claim 1, wherein the sensing electrode comprises platinum and aluminum.

6. The gas sensor of claim 5, wherein the sensing electrode comprises about 96 wt % to about 99.9 wt % platinum, and about 0.1 wt % to about 4 wt % aluminum, based on the total weight of the sensing electrode.

7. The gas sensor of claim 1, wherein the sensing electrode comprises platinum having a grain size of about 2 nm to about 20 nm along a major axis.

8. The gas sensor of claim 1, wherein the sensing electrode further comprises less than or equal to about 2 wt % ruthenium, rhodium, or a combination comprising at least one of the foregoing, based on the total weight of the sensing electrode.

9. The gas sensor of claim 8, wherein the sensing electrode comprises about 0.1 wt % to about 1 wt % ruthenium, rhodium, or a combination comprising at least one of the foregoing, based on the total weight of the sensing electrode.

10. The gas sensor of claim 1, wherein the sensing electrode thickness is of about 0.1 micrometer to about 10 micrometers.

11. The gas sensor of claim 1, wherein the zirconia layer has a porosity of about 2 vol % to about 8 vol %, based on the total volume of the zirconia layer.

12. The gas sensor of claim 1, wherein the protective layer comprises a material selected from the group consisting of spinel, alumina, zirconia, and combinations comprising at least one of the foregoing materials.

13. The gas sensor of claim 1, wherein the protective layer has a thickness of about 140 micrometers to about 240 micrometers.

14. The gas sensor of claim 1, wherein the protective layer has a porosity of about 30 vol % to about 60 vol %, based on the total volume of the protective layer.

* * * * *